(12) United States Patent
Dugar et al.

(10) Patent No.: US 10,898,465 B2
(45) Date of Patent: Jan. 26, 2021

(54) UTILITY OF (+) EPICATECHIN AND THEIR ANALOGS

(71) Applicant: Epirium Bio Inc., San Diego, CA (US)

(72) Inventors: Sundeep Dugar, San Jose, CA (US); George Schreiner, Los Altos Hills, CA (US); Somdutta Sen, Manesar (IN)

(73) Assignee: Epirium Bio Inc., San Diego, CA (US)

( * ) Notice: Subject to any disclaimer, the term of this patent is extended or adjusted under 35 U.S.C. 154(b) by 0 days.

(21) Appl. No.: 16/311,422

(22) PCT Filed: Jun. 21, 2017

(86) PCT No.: PCT/IN2017/050252
§ 371 (c)(1),
(2) Date: Dec. 19, 2018

(87) PCT Pub. No.: WO2017/221269
PCT Pub. Date: Dec. 28, 2017

(65) Prior Publication Data
US 2019/0247359 A1     Aug. 15, 2019

(30) Foreign Application Priority Data

Jun. 21, 2016 (IN) .................. 4200/DEL/2015
Jun. 22, 2016 (IN) .................. 201611021674

(51) Int. Cl.
| | | |
|---|---|---|
| A61K 31/353 | (2006.01) |
| C07D 311/62 | (2006.01) |
| A61P 21/00 | (2006.01) |
| A61P 9/10 | (2006.01) |
| A61P 25/28 | (2006.01) |
| A61P 1/16 | (2006.01) |
| A61P 25/08 | (2006.01) |

(52) U.S. Cl.
CPC .............. *A61K 31/353* (2013.01); *A61P 1/16* (2018.01); *A61P 9/10* (2018.01); *A61P 21/00* (2018.01); *A61P 25/08* (2018.01); *A61P 25/28* (2018.01); *C07D 311/62* (2013.01)

(58) Field of Classification Search
CPC .................................................... A61K 31/353
USPC ........................................................ 549/399
See application file for complete search history.

(56) References Cited

U.S. PATENT DOCUMENTS

| | | |
|---|---|---|
| 3,689,663 A | 9/1972 | Kramer |
| 4,334,067 A | 6/1982 | Ohno |
| 5,648,331 A | 7/1997 | Koudsi |
| 6,191,109 B1 | 2/2001 | Besner |
| 9,187,448 B2 | 11/2015 | Becker |
| 9,428,482 B2 | 8/2016 | Dugar |
| 9,556,140 B2 | 1/2017 | Dugar |
| 9,901,564 B2 | 2/2018 | Schreiner |
| 10,052,316 B2 | 8/2018 | Villarreal |
| 2003/0166583 A1 | 9/2003 | Yoa-pu |
| 2010/0048920 A1 | 2/2010 | Romanczyk, Jr. |
| 2010/0168221 A1 | 7/2010 | Lee |
| 2010/0266523 A1 | 10/2010 | Vercauteren |
| 2013/0171268 A1 | 7/2013 | Villarreal |
| 2014/0031421 A1 | 1/2014 | Dugar |
| 2014/0256741 A1 | 9/2014 | Becker |
| 2015/0080328 A1 | 3/2015 | Villarreal |
| 2015/0368223 A1 | 12/2015 | Dugar |
| 2018/0193306 A1 | 7/2018 | Schreiner |
| 2019/0046517 A1 | 2/2019 | Villarreal |
| 2019/0247359 A1 | 8/2019 | Dugar |
| 2019/0262347 A1 | 8/2019 | Dugar |

FOREIGN PATENT DOCUMENTS

| | | |
|---|---|---|
| CN | 102503924 A | 6/2012 |
| CN | 102578094 A | 7/2012 |
| EP | 0618203 A1 | 10/1994 |
| EP | 1849779 A1 | 10/2007 |
| JP | S5663981 A | 5/1981 |
| JP | 57118580 | * 7/1982 |
| JP | H06279430 A | 10/1994 |
| JP | 2001131169 A | 5/2001 |
| JP | 2005531596 A | 10/2005 |
| JP | 2006249056 A | 9/2006 |

(Continued)

OTHER PUBLICATIONS

Agranat, I. et al. (Oct. 2002). "Putting Chirality to Work: The Strategy of Chiral Switches," Nature Reviews Drug Discovery 1:753-768.

(Continued)

*Primary Examiner* — Taofiq A Solola
(74) *Attorney, Agent, or Firm* — Morrison & Foerster LLP

(57) ABSTRACT

The present invention pertains to the enhanced activity of (+) epicatechin over (−) epicatechin. The present invention is related to novel analogs of (+) epicatechin of the formula (I), which enhances the pharmacokinetics and therefore the pharmacodynamics of (+) epicatechin. The present invention is related to analogs of (+) epicatechin of the formula (I). The general structure of the analogs of the present invention may be represented by Formula (I): Formula (I) wherein A and B are independently OR1 and C and D are independently OH; wherein R1 is independently C1 to C10 lower straight or branched chain acyclic or cyclic alkyl, or is selected from the group comprising, hydroxy butyric acid, dichloroacetic acid; phenyl butyric acid; valproic acid.

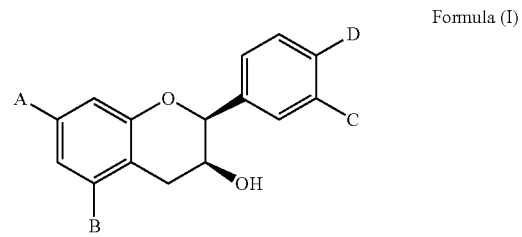

Formula (I)

10 Claims, 3 Drawing Sheets

(56) References Cited

FOREIGN PATENT DOCUMENTS

| | | |
|---|---|---|
| JP | 2008505657 A | 2/2008 |
| JP | 2008156324 A | 7/2008 |
| JP | 2009501706 A | 1/2009 |
| JP | 2010155840 A | 7/2010 |
| JP | 2011503171 A | 1/2011 |
| JP | 2012524077 A | 10/2012 |
| WO | WO2003101927 A1 | 12/2003 |
| WO | WO2005034976 A1 | 4/2005 |
| WO | WO2006010117 A2 | 1/2006 |
| WO | WO2006049258 A1 | 5/2006 |
| WO | WO2006010117 A3 | 6/2006 |
| WO | WO2007002877 A1 | 1/2007 |
| WO | WO2007126293 A1 | 11/2007 |
| WO | WO2010121232 A1 | 10/2010 |
| WO | WO2012101652 A2 | 8/2012 |
| WO | WO2012101652 A3 | 12/2012 |
| WO | WO2012170430 A1 | 12/2012 |
| WO | WO2013020979 A1 | 2/2013 |
| WO | WO2013022846 A2 | 2/2013 |
| WO | WO2013142816 A1 | 9/2013 |
| WO | WO2013022846 A3 | 10/2013 |
| WO | WO2014115174 A2 | 7/2014 |
| WO | WO2014162320 A2 | 10/2014 |
| WO | WO2014115174 A3 | 12/2014 |
| WO | WO2014162320 A3 | 12/2014 |
| WO | WO2016013030 A2 | 1/2016 |
| WO | WO2016013030 A3 | 1/2016 |
| WO | WO2018083713 A1 | 5/2018 |
| WO | WO2019164914 A1 | 8/2019 |

OTHER PUBLICATIONS

Baba, S. et al. (2001). "In Vivo Comparison of the Bioavailability of (+)-Catechin, (-)-Epicatechin and Their Mixture in Orally Administered Rats," J. Nutr. 131:2885-2891.

Baba, S. et al. (Nov. 2000). "Bioavailability of (-)-epicatechin Upon Intake of Chocolate and Cocoa In Human Volunteers," Free Radic. Res. 33(5):635-641.

Basak, A. et al. (Sep. 1, 2008, e-pub. Jul. 17, 2008). "Studies on the Porcine Liver Esterase-Catalyzed Hydrolysis of Pentaacetyl Catechin and Epicatechin: Application to the Synthesis of Novel Dimers and Trimers," Bioorganic & Medicinal Chemistry Letters 18(17):4900-4903.

Bergot, B.J. et al. (1965). "Anthocyanins and Related Compounds. V. Formation of Bisflavenylidenes From Flavones by Reductive Dimerization," Tetrahedron 21(3):657-661.

Brent, J.A. et al. (1992). "Role of Free Radicals in Toxic Hepatic Injury II. Are Free Radicals the Cause of Toxin-Inducted Liver Injury?" J. Toxicol. Clin. Toxicol. 31:173-196.

Brown, B.R. et al. (1974). "Reactions of Flavanoids and Condensed Tannins With Sulphur Necleophiles," J. Chem. Soc. Perkin Trans. 1 pp. 2036-2049.

Caldwell, J. (Jul./Aug. 1999). "Through the Looking Glass in Chiral Development," Modern Drug Discov 2:51-60.

CAS Registry No. 1391392-14-5, (Aug. 15, 2012), AlphaChiron Biochemicals, LLC, 1 page.

Clark-Lewis, J.W. et al. (1973). "Chemistry of 3-oxoflavans: Oxidation of (+)-Catechin 5,7,3',4'-Tetramethyl Ether to (+)-5,7,3',4'-Teramethoxy-3-Oxoflavan," Australian Journal of Chemistry 26(12):2675-2682.

Crawford, E.S. et al. (1986). "Thoracoabdominal Aortic Aneurysms: Preoperative and Intraoperative Factors Determining Immediate and Long-Term Results of Operation in 605 Patients," J. Vas. Surg. 3:389-404.

Cushnie, T.P.T. et al. (Nov. 1, 2008). "Investigation of the Antibacterial Activity of 3-O-octanoyl-(-)-epicatechin," J. Applied Microbiology 105(5):1461-1469.

Extended European Search Report, dated Jun. 27, 2016, for European Patent Application No. 14778691.7, 7 pages.

Extended European Search Report, dated Nov. 26, 2014, for European Patent Application No. 12821887.2, 7 pages.

Ferrari, G.V. et al. (2010, e-pub. May 25, 2010). "Novel Synthesis of 3,3'-Dihydroxyflavone and Apparent Formation Constants of Flavonoid-Ga(III) Complexes," J. Chemical & Engineering Data 55(9):3080-3083.

Gebicki, S. et al. (1999). "Crosslinking of DNA and Proteins Induced by Protein Hydroperoxides," Biochem. J. 338:629-636.

International Preliminary Report on Patentability, dated Dec. 25, 2018, for PCT Application No. PCT/IN2017/050252, filed Jun. 21, 2017, 6 pages.

International Preliminary Report on Patentability, dated Feb. 11, 2014, for PCT Application No. PCT/US2012/049767, filed Aug. 6, 2012, 7 pages.

International Preliminary Report on Patentability, dated Oct. 6, 2015, for PCT Application No. PCT/IN2014/000213, filed Apr. 4, 2014, 9 pages.

International Search Report and Written Opinion, dated Jun. 28, 2018, for PCT Application No. PCT/US2012/049767, filed Aug. 6, 2012, 7 pages.

International Search Report and Written Opinion, dated Sep. 2, 2014, for PCT Application No. PCT/IN2014/000213, filed Apr. 4, 2014, 14 pages.

International Search Report and Written Opinion, dated Sep. 22, 2017 for PCT Application No. PCT/IN2017/050252, filed Jun. 21, 2017, 8 pages.

Kouchoukos, N.T. et al. (1990). "Elective Hypothermic Cardiopulmonary Bypass and Circulatory Arrest for Spinal Cord Protection During Operations on the Thoracoabdominal Aorta," J. Thorac. Cardiovasc. Surg. 99:659-664.

Lecanu, L. et al. (Feb. 16, 1998). "Deleterious Ca-Independent NOS Activity After Oxidative Stress in Rat Striatum," Neuroreport 9(3):559-663.

Li, Z. et al.(Dec. 15, 2008, e-pub. Oct. 11, 2008). "Synthesis of a Library of Glycosylated Flavonols," Tetrahedron Letters 49(51):7243-7245.

Lin, Y.-M. et al. (2002). "Chalcones and Flavonoids as Anti-Tuberculosis Agents," Bioorganic & Medicinal Chemistry 10:2795-2802.

Maloney, D.J. et al. (2005). "(+)-Myristinin A, a Naturally Occurring DNA Polymerase β Inhibitor and Potent DNA-Damaging Agent," J. Am. Chem. Soc. 127(12):4140-4141.

Mewett, K.N. et al. (2009, e-pub. Sep. 4, 2009). "Synthesis and Biological Evaluation of Flavan-3-ol Derivatives as Positive Modulator of GABAA Receptors," Bioorganic & Medicinal Chemistry 17:7156-7173.

Moini, H. et al. (Feb. 15, 1999). "Bioflavonoid Effects on the Mitochondrial Respiratory Electron Transport Chain and Cytochrome c Redox State," Redox Report 4(1-2):35-41.

Nel et al. (1999). "The Novel Flavan-3-ol, (2R,3S)-guibortinidol and Its Diastereomers," Phytochemistry 52:1153-1158.

Obata, T. (Jul. 1997). "Use of Microdialysis for In-Vivo Monitoring of Hydroxyl Free-Radical Generation in the Rat," J. Pharm. Pharmacol. 49(7):724-730.

Peng, W. et al. (2009, epub. May 28, 2009). "Deuterium Labelling of Theaflavin," J. Label. Compd. Radiopharm. 52:312-315.

Pereira, C.V. et al. (2009)."Investigating Drug-induced Mitochondrial Toxicity: A Biosensor to Increase Drug Safety?" Current Drug Safety 4(1):1-22.

Reiter, R.J. et al. (1998). "Reactive Oxygen Intermediates, Molecular Damage, and Aging: Relation to Melatonin," Ann. N.Y. Acad. Sci. 854:410-424.

Remington: The Science and Practice of Pharmacy, 21st Edition , Journal of Pharmacy Technology, Mar.-Apr. 2006, 22:133-135.

Rensburg, H.V. et al. (1997). "Enantioselective Synthesis of Flavonoids, Part3. Trans- and cis-Flavan-3ol Methyl Ether Acetates," J. Chem. Soc. Perkin Trans 1 pp. 3415-3421.

Rizzo, A.F. et al. (Mar. 1994). "Protective c DON or T-2 Toxin," Zentralbl. Veterinarmed A. 41(2):81-90.

Saini, T. et al. (Sep. 1998). "Protective Ability of Acetylsalicylic Acid (aspirin) to Scavenge Radiation Induced Free Radicals in J774A.1 Macrophage Cells," Res. Comm. Mol. Pathol. Pharmacol. 101(3):259-268.

(56) References Cited

OTHER PUBLICATIONS

Shadkami, F. et al. (May 2009, e-pub. Sep. 27, 2008). "Analysis of Catechins and Condensed Tannins by Thermally Assisted Hydrolysis/Methylation-GC/MS and by a Noveal Two Step Methylation," J. Analytical and Applied Pryolysis, 85(1+2)54-65.

Smith et al. (2011). "5-Deozyflavan-3-ol-Based Proanthocyanidins With Antinutritional and Antimicrobial Properties From the Forage Legume Acaciella angustissima," J. Applies Botany and Food Quality 84:142-150.

Smith, S. (2009, e-pub. May 4, 2009). "Chiral Toxicology; It's the Same Only Different," Toxicological Sciences 110 (1):4-30.

Starp, C. et al. (2006, e-pub. Nov. 8, 2005). "Characteristics of (+)-catechin and (-)-epicatechin Transport Across Pig Intestinal Brush Border Membranes," Ann. Nutr. Metab. 50(1):59-65.

U.S. Appl. No. 15/419,406, Dugar et al., filed Jan. 30, 2017.(not submitted herewith pursuant to the waiver of 37 C.F.R. § 1.98(a)(2)(iii) issued by the Office on Sep. 21, 2004).

U.S. Appl. No. 16/742,608, Schreiner et al., filed Jan. 14. 2020.(not submitted herewith pursuant to the waiver of 37 C.F.R. § 1.98(a)(2)(iii) issued by the Office on Sep. 21, 2004).

Ejaz A.M. et al. (Feb. 11, 2013). "Amelioration of Cognitive Impairment and Neurodegeneration by Catechin Hydrate in Rat Model of Streptozotocininduced Experimental Dementia of Alzheimer's Type," Neurochemistry International, 62(4):492-501, 46 pages.

Extended European Search Report, dated Jan. 27, 2020, for European Patent Application No. 17814912.6, 10 pages.

Fukumitsu. (1960). "Influences of Adrenochrome Derivatives and Flavonoids on Chline Acetylase and Histidine Decarboxylase," Tasihitsu Igaku Kenyusho Hokoku 11:137-161. Abstract Copy, 2 pages.

* cited by examiner

UTILITY OF (+) EPICATECHIN AND THEIR ANALOGS

FIELD OF THE INVENTION

The present invention discloses the utility of (+) epicatechin and analogs of (+) isoform of epicatechin.

BACKGROUND OF INVENTION

Polyphenolic natural products are important because of their utility in various biological pathways, their occurrence in foodstuffs, and hence their relevance for human health. The stereochemistry of the substituents on a polyphenol monomeric unit of a polyphenol may be described in terms of their relative stereochemistry, "alpha/beta" or "cis/trans". The term "alpha" ( ) indicates that the substituent is oriented above the plane of the flavanol ring, whereas, "beta" ( ) indicates that the substituent is oriented above the plane of the ring. The term "cis" indicates that two substituents are oriented on the same face of the ring, whereas "trans" indicates that two substituents are oriented on opposite faces of the ring.

Catechins possess two benzene rings and a dihydropyran heterocycle (the C-ring) with a hydroxyl group on carbon 3. A ring is similar to a resorcinol moiety while the B ring is similar to a catechol moiety. There are two chiral centers on the molecule, on carbons 2 and 3. Therefore, it has four diastereoisomers. Two of the isomers are in a trans configuration and are called catechin and the other two are in a cis configuration and are called epicatechin.

(+)-Catechin and (−)-epicatechin are the most abundant naturally occurring epimers in cacao. During biosynthesis catechin and epicatechin are predominantly synthesized as (+)-catechin and (−)-epicatechin. However, certain plants such as spotted knapweed (*Centaurea maculosa*, Lam.) demonstrate the presence of racemic catechin and both (+/−)-catechin and (+/−)-epicatechin was described in guaraná seeds (*Paullinia cupana* var. *sorbilis*).

Since, catechin and epicatechin possess two chiral centers; their properties depend on the conformation of the molecules. Since (−)-epicatechin, is the predominantly synthesized or available epimer of epicatechin in cacao or tea, most of the reports of the biological activity tested are for this isomer. The activity of epicatechins as their individual epimers and/or racemic mixture is not well documented in prior art. The prior art discloses that naturally occurring member of the flavonoid family, (−)-epicatechin as inducing mitochondrial biogenesis in vitro and in vivo, resulting in the successful treatment of diseases associated with mitochondrial depletion, such as muscular dystrophy. Numerous papers and patents discuss the broad use of flavonoids as anti-oxidants or anti-cancer agents. Those teaching this art do not distinguish chiral flavonoids as being uniquely active. Nor has there been any report of stereo selective properties of a unique flavonoid. Rather their effects have typically been described as attributable to all members of the flavonoid class. There are reports in prior art that state that (−) isoform of epicatechin, found naturally occurring in cocoa, green tea, and other plant sources of polyphenols, can prevent acute mitochondrial injury involving the formation of mitochondrial permeability transition pores that damage mitochondrial function by allowing the non-specific diffusion of electrolytes into the mitochondria and that (−)-isoform of epicatechin is capable of inducing mitochondrial biogenesis in in vivo models (see WO 2012/170430 and WO 2013/142816). The differences in the activities between the isomers are also not known and documented in the prior art.

Isolation and availability of pure polyphenols from natural sources is difficult with increasing degree of oligomerization and has been one of the reasons for the lack of information about the stereochemical difference of activity of the enantiomers of epicatechin and therefore synthesis of polyphenols is preferred. In addition, such polyphenols have certain drawbacks, when used clinically, such as, poor pharmacokinetic profile. Hence there is a need to improve the pharmacokinetic profiles of the polyphenols.

One of the consequences of a means of production of a synthetic epimer is the ability to construct new chemical analogues of a stereochemically defined phenol. The analogues of polyphenols may be used, to improve the pharmacokinetic profile of the polyphenol by, increasing the half-life of the parent drug, which would help decrease the number of doses needed to achieve a desired effect, and/or create a more effective and/or a safer drug.

There are certain prior art drawn to the analogs of epicatchin, WO 2014/162320, the Applicant disclosed certain novel analogs of natural flavonoid phenols, that were biologically active, but the Application, neither discloses the importance of stereoisoforms in activity, nor does the application disclose the mode of activity of these analogs.

Hence, there is a need to examine the utility of the isomers of catechin/epicatechin and also for novel analogs of epicatechin that effectively delivers the preferred isomer.

OBJECT OF THE INVENTION

An object of the invention is to examine the utility of the isomers of epicatechin and also to provide novel analogs of epicatechin that effectively delivers the preferred isomer

BRIEF DESCRIPTION

Figure 1:
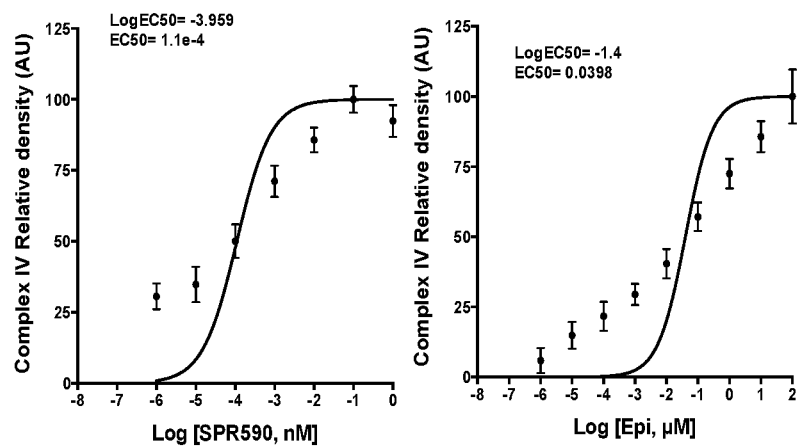
FIG. 1: depicts the activity of (+)-epicatechin in inhibition complex IV on the increase of the expression of Electron Transport Chain TV (ETC TV) in comparison to (−) epicatechin, (+)-epicatechin is approximately 400 fold more potent than (−)-epicatechin—an unprecedented gain of biological potency.

The present invention pertains to the enhanced activity of (+) epicatechin over (−) epicatechin.

The present invention is related to novel analogs of (+) epicatechin of the formula (I), which enhances the pharmacokinetics and therefore the pharmacodynamics of (+) epicatechin.

The present invention is related to analogs of (+) epicatechin of the formula (I). The general structure of the analogs of the present invention may be represented by Formula (I):

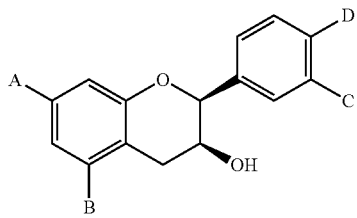

Formula (I)

wherein A and B are independently $OR_1$ and C and D are independently OH; wherein $R^1$ is independently $C_1$ to $C_{10}$ lower straight or branched chain acyclic or cyclic alkyl, or is selected from the group comprising, hydroxy butyric acid. dichloroacetic acid; phenyl butyric acid; valproic acid.

The present invention discloses analogs of (+) epicatechin of the formula (I), wherein B is $OR_1$ and A, C and D me independently OH: wherein $R^1$ is independently $C_1$ to $C_{10}$ lower straight or branched chain acyclic or cyclic alkyl, or is selected from the group comprising, L-Glutamic acid, hydroxy butyric acid, dichloroacetic acid; phony butyric acid; valproic acid.

The present invention includes a process for preparation of compounds of the present invention and methods of use comprising the compounds of the present invention.

DETAILED DESCRIPTION

The present invention is based on the unexpected stereo selectivity with respect to the isomers of epicatechin, which has two enantiomers. (−)-epicatechin, and (+)-epicatechin.
A. Activity of (+) Epicatechin Compared to (−)Epicatechin The physical and biochemical properties of stereo isomers can differ significantly and unexpectedly. Enantiomers can differ with respect to activity and physicochemical properties. Stereo selective metabolism of chiral compounds can influence pharmacokinetics, pharmacodynamics, and toxicity. There is no predictability with respect to differential expression of therapeutic or adverse effects among enantiomers (Agranat I et al 2002 Putting chirality to work: the strategy of chiral switches. Nature Reviews Drug Discovery 1:753-768; When one enantiomer has activity of interest, its paired enantiomer typically is either inactive, or an antagonist of the active enantiomer, or has a separate activity that could be undesirable. There is no way to predict or anticipate such outcomes for any given enantiomer (Caldwell, J, 1999, Through the looking glass in chiral development. Modern Drug Discov 2:51-60). Occasionally both enantiomers may show similar activities to varying degrees. It is more usual to see the greatest degree of variability among the enantiomers of receptor antagonists, as there are many potential ways to sterically obstruct the active site of a receptor. The largest therapeutic variation in potency that we have been able to determine among enantiomers, therefore, are receptor antagonists For example, S (−)-propranol exhibits 100-fold greater receptor antagonism than the R-(+)-propranolol with respect to blocking the 1, 2, and 3 adrenergic receptors. (Smith, S, 2009, Chiral toxicology; it's the same only different ToxicolSci 110:4-30). The more restricted requirement of optimal ligand fit to a receptor to activate the receptor normally results in much smaller variation with respect to potency of receptor activation. When paired enantiomers exhibit similar agonist activity, the differences in potency are typical those of a fractional ratio. The prior art does not disclose any examples of differential agonist activity of enantiomers of more than a few fold.

The present invention discloses a remarkable range of biological activity across the two enantiomers of epicatechin, something heretofore not described for flavonoids as a class. The enantiomer of (−)-epicatechin is (+)-epicatechin. When compared in an assay on the increase of the expression of Electron Transport Chain IV (ETC IV), (+)-epicatechin is approximately 400 fold more potent than (−)-epicatechin—an unprecedented gain of biological potency (FIG. 1). The data is represented at Table 1:

TABLE 1

$EC_{50}$ (mM) OF COMPOUNDS ON MITOCHONDRIAL ETC COMPLEXES

| Compound | ELCTRON TRANSPORT CHAIN COMPLEX IV |
|---|---|
| (−)-Epicatechin | 0.04 |
| (+)-Epicatechin | 0.0001 |

The basis for the advantageous properties of the (−)- and (+)-isoforms of epicatechin consists of their structural homology to recently discovered hormone that mediates which is set out in the patent application PCT/IN2015/050072:

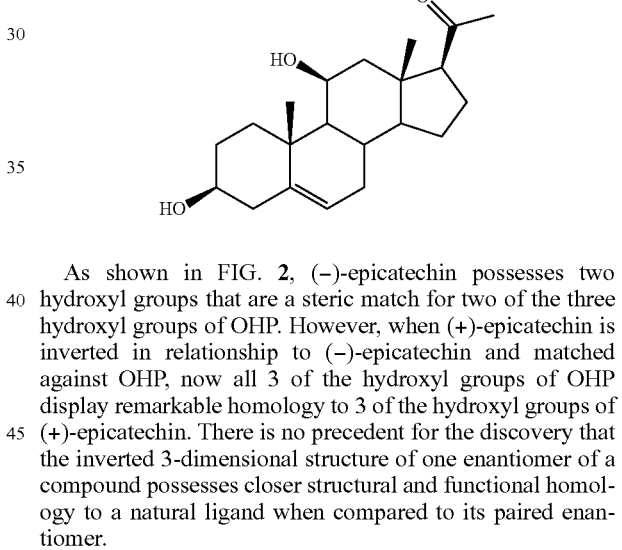

Figure 2:
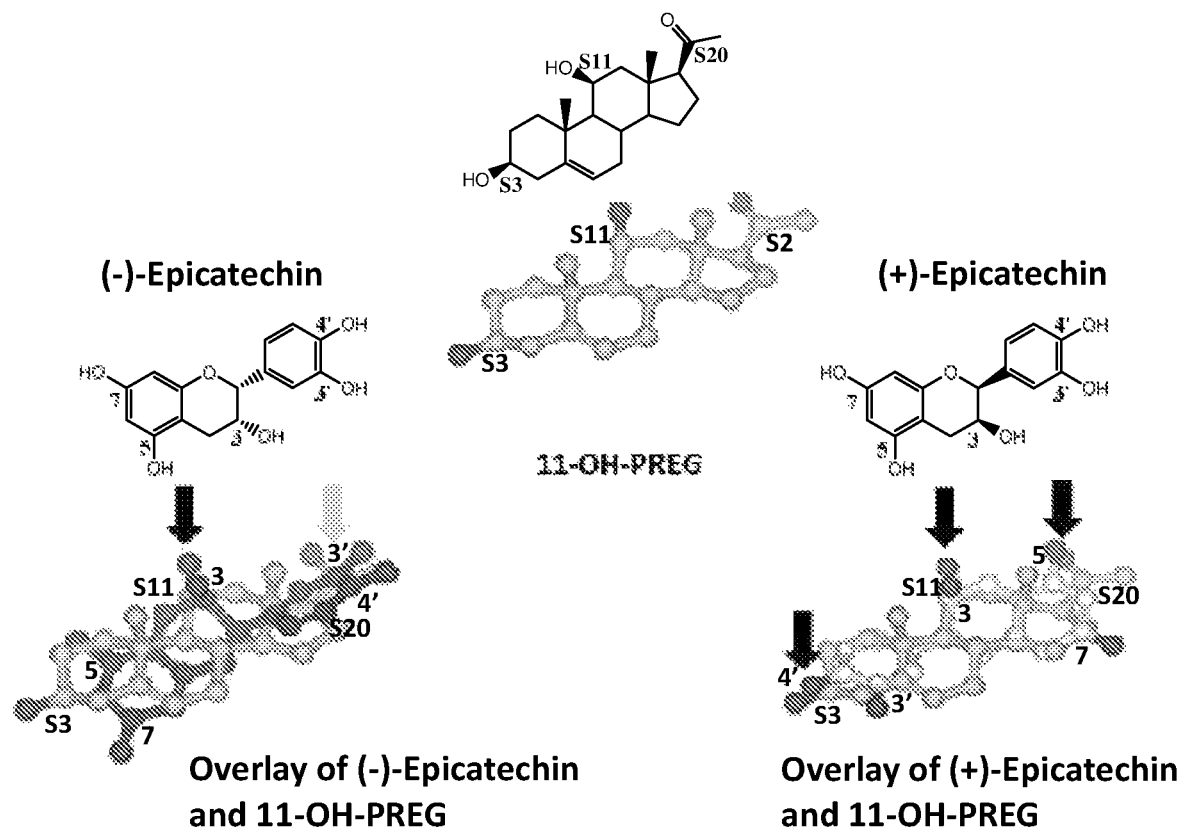
FIG. 2: depicts the greater homology to 11-beta-hydroxy-pregnenolone of (+)-epicatechin compared to that of (−)-epicatechin.

As shown in FIG. 2, (−)-epicatechin possesses two hydroxyl groups that are a steric match for two of the three hydroxyl groups of OHP. However, when (+)-epicatechin is inverted in relationship to (−)-epicatechin and matched against OHP, now all 3 of the hydroxyl groups of OHP display remarkable homology to 3 of the hydroxyl groups of (+)-epicatechin. There is no precedent for the discovery that the inverted 3-dimensional structure of one enantiomer of a compound possesses closer structural and functional homology to a natural ligand when compared to its paired enantiomer.

Therefore, the preferred enantiomer of epicatechin for use is the (+) isoform or the (2S,3S) enantiomer of epicatechin and its analogs, preferably free of contamination with catechin. (+)-Epicatechin results in a superior pharmacological effect when free from other flavonoids, particularly from known isomers of epicatechin.

Without being limited by theory, it is submitted that the compounds of the present invention are active due to their unique configuration and stereochemistry. The compounds of the present invention are useful in treating diseases or disorders that would benefit from modification of Electron transfer Chain (ETC) and particularly electron transfer chain IV.

The present invention provides methods for treating diseases or disorders that would benefit from increased expression of Electron transfer Chain, particularly ETC IV. The methods involve administering to a subject in need thereof a therapeutically effective amount of a (+)-epicatechin.

The vast majority of the body's need for ATP is supplied through the process of oxidative phosphorylation, carried out in the mitochondria in all tissues. There are 5 protein complexes, known as the Electron Transport Complexes that effect ATP synthesis. ETC I, II, III and IV mediate electron transport. ETC I, III and IV also function as proton pumps that maintain an electrochemical gradient necessary for activity of ETC V, the ATP synthase enzyme that makes ATP from ADP. Complex IV, also known as cytochrome c oxidase, (COX), consists of 14 subunits whose assembly into a functional complex requires an additional 30 protein factors. ETC IV is particularly important to oxidative phosphorylation. It is the only one of the ETC complexes to manifest tissue-specific and developmentally regulated isoforms, allowing precise regulation of oxidative phosphorylation under a variety of metabolic demands. Thus the ETC IV (COX) protein complex is considered to be the rate-limiting step in oxidative phosphorylation. Small positive or negative changes in ETC IV can exert a significant impact on health, Selective activation of COX activity has been associated with improved cognition, improved neuronal cell survival under stress, and improved wound healing. Mutations in the numerous proteins that comprise or regulate the activity of ETC IV reveal the pathological consequences of even modest decreases in ETC IV activity. As little as a 30% reduction in COX activity has been shown to induce cardiomyopathy or be associated with the development of neurodegenerative diseases such as Alzheimer's. Decreases in COX (ETC IV) expression due to mutations or molecular manipulation have been associated with loss of muscle endurance and speed, muscle dystonia, immunodeficiency states due to impaired T cell maturation, cardiomyopathy, particularly of the aging phenotype, ataxia, neurodegeneration, increased toxicity in the setting of ischemia, pulmonary inflammation and fibrosis, encephalopathy, vascular insufficiency, and stimulation of cancer cell proliferation. Additional specific diseases associated with COX subunit isoform mutations causing loss of function include exocrine pancreatic insufficiency, inflammatory lung disease, Charcot-Marie-Tooth disease, infantile encephalomyopathy, and Leigh syndrome neurodegeneration with epilepsy.

In summary, the following conditions associated with loss of COX expression or function would be expected to be therapeutically responsive to a potent, preferential inducer of COX (ETC IV) expression: impaired cognition, neurodegenerative diseases such as Alzheimer's or Leigh syndrome, dystonia, sarcopenia, cardiomyopathy of aging or other diseases associated with mitochondrial dysfunction, ischemic vascular disease, immunodeficiency states, ataxia, pulmonary inflammation and fibrosis, infantile encephalomyopathy, epilepsy. Charcot-Marie-Tooth disease, exocrine pancreatic insufficiency, impaired wound healing, growth of cancer cells.

In addition, given the relative effect of (+)-epicatechin compared to (−)-epicatechin in lowering the elevated triglycerides of mice on a high fat diet, (+)-epicatechin and its analogs would be the preferred medicament for conditions associated with elevated triglycerides, such as metabolic syndrome, Type II diabetes, congenital hyperlipidemias, and drug-induced hyperlipidemia, as is observed with corticosteroid treatments.

B. Analogs of (+) Epicatechin with Increased Pharmacokinetic Property and Enhanced Utility.

In another aspect, the present application also discloses compounds of formula (I) that are analogs of (+)-epicatechin that possess improved pharmacokinetic properties and enhanced utility.

The general structure of the analogs of the present invention may be represented by Formula (I):

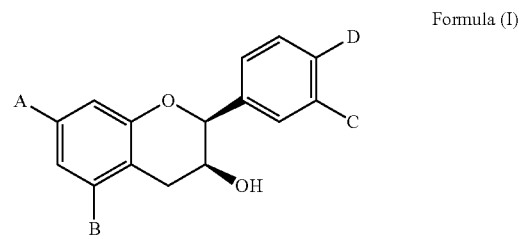

Formula (I)

Formula (I) wherein A and B are independently OR1 and C and D are independently OH; wherein $R^1$ is independently $C_1$ to $C_{10}$ lower straight or branched chain acyclic or cyclic alkyl, or is selected from the group comprising, hydroxy butyric acid, dichloroacetic acid; phenyl butylic add; valproic acid.

The present invention discloses analogs of (+) epicatechin of the formula (I), wherein B is $OR_1$ and A, C and D are independently OH; wherein $R^1$ is independently $C_1$ to $C_{10}$ lower straight or branched chain acyclic or cyclic alkyl, or is; elected from the group comprising, L-Glutamic acid, hydroxy butyric acid, dichloroacetic acid; phenyl butyric acid; valproic acid.

A few illustrative compounds of the present invention are listed at Table 2.

TABLE 2

Illustrative Compounds of the Present Invention.

| S. No. | Structure | IUPAC Name |
|---|---|---|
| 1001 | 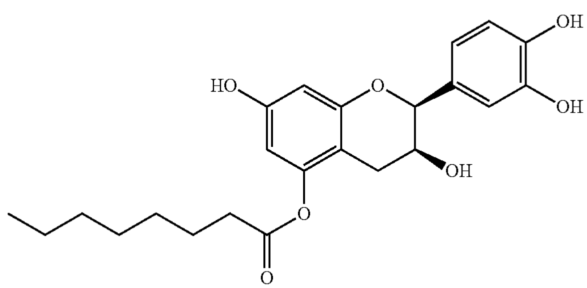 [SMILES: CCCCCCCC(=O)Oc1cc(O)cc2c1C[C@H](O)[C@H](c1ccc(O)c(O)c1)O2] | (2S,3S)-2-(3,4-dihydroxyphenyl)-3,7-dihydroxychroman-5-yl octanoate |

TABLE 2-continued

Illustrative Compounds of the Present Invention.

| S. No. | Structure | IUPAC Name |
|---|---|---|
| 1002 | 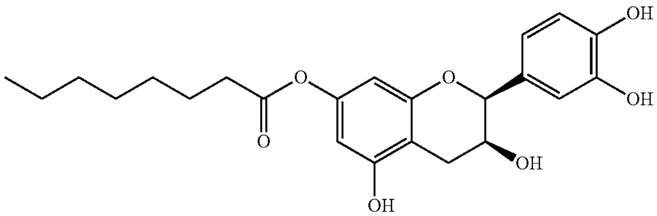 [SMILES: CCCCCCCC(=O)Oc1cc(O)c2c(c1)O[C@@H](c1ccc(O)c(O)c1)[C@@H](O)C2] | (2S,3S)-2-(3,4-dihydroxyphenyl)-3,5-dihydroxychroman-7-yl octanoate |
| 1003 | 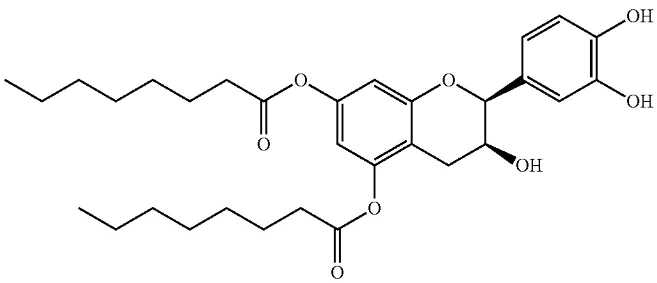 [SMILES: CCCCCCCC(=O)Oc1cc(OC(=O)CCCCCCC)c2c(c1)O[C@@H](c1ccc(O)c(O)c1)[C@@H](O)C2] | (2S,3S)-2-(3,4-dihydroxyphenyl)-3-hydroxychroman-5,7-diyl dioctanoate |
| 1004 | 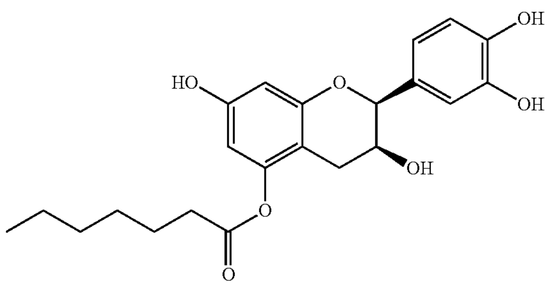 [SMILES: CCCCCCC(=O)Oc1cc(O)cc2c1C[C@H](O)[C@H](c1ccc(O)c(O)c1)O2] | (2S,3S)-2-(3,4-dihydroxyphenyl)-3,7-dihydroxychroman-5-yl heptanoate |
| 1005 | 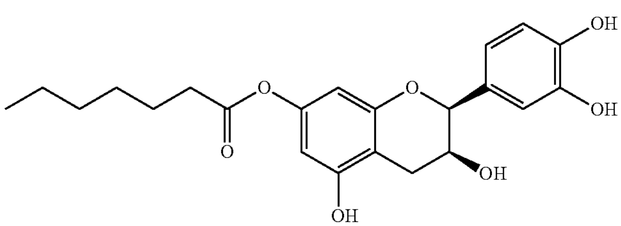 [SMILES: CCCCCCC(=O)Oc1cc(O)c2c(c1)O[C@@H](c1ccc(O)c(O)c1)[C@@H](O)C2] | (2S,3S)-2-(3,4-dihydroxyphenyl)-3,5-dihydroxychroman-7-yl heptanoate |
| 1006 | 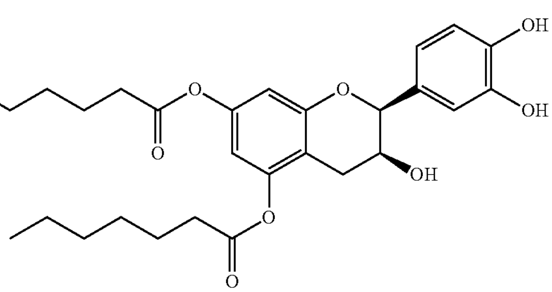 | (2S,3S)-2-(3,4-dihydroxyphenyl)-3-hydroxychroman-5,7-diyl diheptanoate |

TABLE 2-continued

Illustrative Compounds of the Present Invention.

| S. No. | Structure | IUPAC Name |
| --- | --- | --- |
| 1007 | 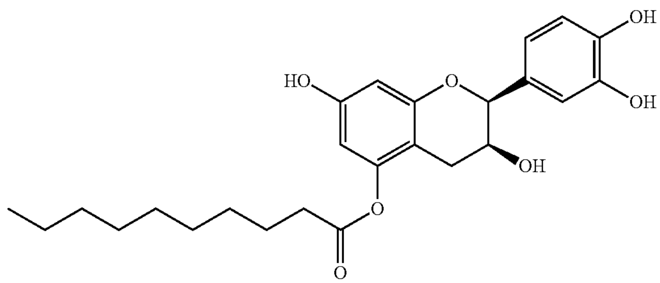 [SMILES: CCCCCCCCCC(=O)Oc1cc(O)cc2c1C[C@H](O)[C@H](c1ccc(O)c(O)c1)O2] | (2S,3S)-2-(3,4-dihydroxyphenyl)-3,7-dihydroxychroman-5-yl decanoate |
| 1008 | 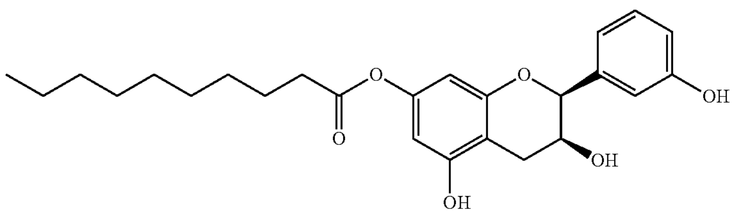 [SMILES: CCCCCCCCCC(=O)Oc1cc(O)c2c(c1)O[C@@H](c1cccc(O)c1)[C@@H](O)C2] | (2S,3S)-2-(3,4-dihydroxyphenyl)-3,5-dihydroxychroman-7-yl decanoate |
| 1009 | 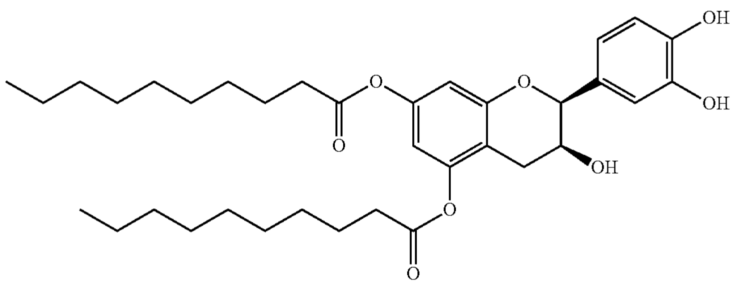 [SMILES: CCCCCCCCCC(=O)Oc1cc(OC(=O)CCCCCCCCC)c2c(c1)O[C@@H](c1ccc(O)c(O)c1)[C@@H](O)C2] | (2S,3S)-2-(3,4-dihydroxyphenyl)-3-hydroxychroman-5,7-diyl bis(decanoate) |
| 1010 | 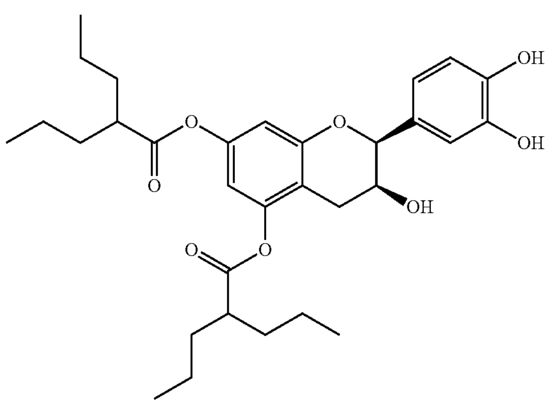 [SMILES: CCCC(CCC)C(=O)Oc1cc(OC(=O)C(CCC)CCC)c2c(c1)O[C@@H](c1ccc(O)c(O)c1)[C@@H](O)C2] | (2S,3S)-2-(3,4-dihydroxyphenyl)-3-hydroxychroman-5,7-diyl bis(2-propylpentanoate) |
| 1011 | 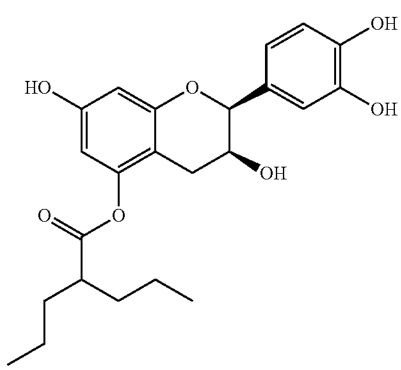 [SMILES: CCCC(CCC)C(=O)Oc1cc(O)cc2c1C[C@H](O)[C@H](c1ccc(O)c(O)c1)O2] | (2S,3S)-2-(3,4-dihydroxyphenyl)-3,7-dihydroxychroman-5-yl 2-propylpentanoate |

TABLE 2-continued

Illustrative Compounds of the Present Invention.

| S. No. | Structure | IUPAC Name |
| --- | --- | --- |
| 1012 | 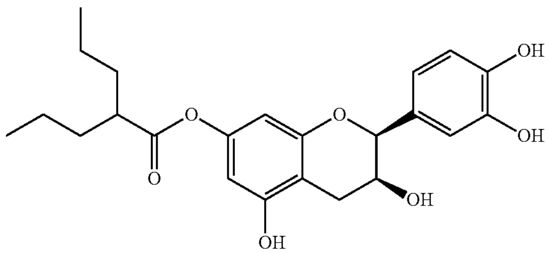 [SMILES: CCCC(CCC)C(=O)Oc1cc(O)c2c(c1)O[C@@H](c1ccc(O)c(O)c1)[C@@H](O)C2] | (2S,3S)-2-(3,4-dihydroxyphenyl)-3,5-dihydroxychroman-7-yl 2-propylpentanoate |
| 1013 | 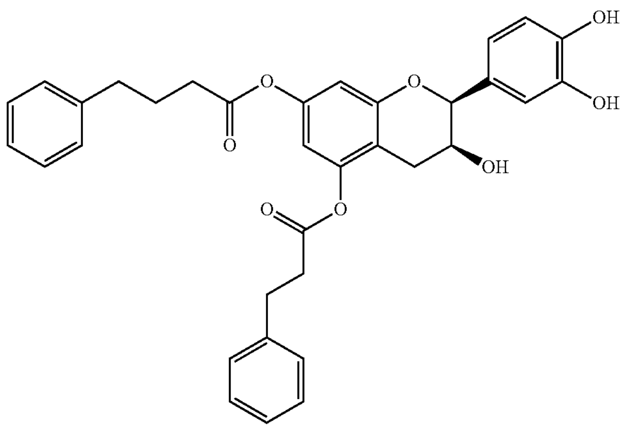 [SMILES: O=C(CCCc1ccccc1)Oc1cc(OC(=O)CCc2ccccc2)c2c(c1)O[C@@H](c1ccc(O)c(O)c1)[C@@H](O)C2] | (2S,3S)-2-(3,4-dihydroxyphenyl)-3-hydroxy-5-((3-phenylpropanoyl)oxy)chroman-7-yl 4-phenylbutanoate |
| 1014 | 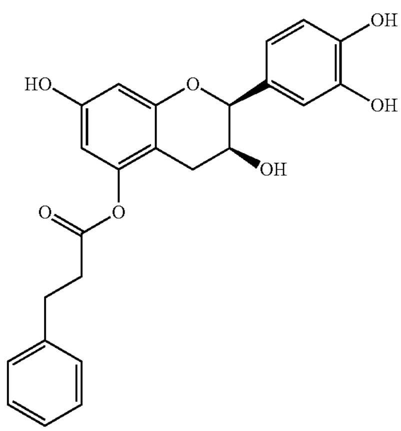 [SMILES: O=C(CCc1ccccc1)Oc1cc(O)cc2c1C[C@H](O)[C@H](c1ccc(O)c(O)c1)O2] | (2S,3S)-2-(3,4-dihydroxyphenyl)-3,7-dihydroxychroman-5-yl 3-phenylpropanoate |
| 1015 | 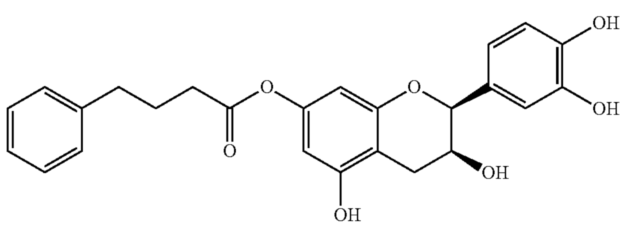 [SMILES: O=C(CCCc1ccccc1)Oc1cc(O)c2c(c1)O[C@@H](c1ccc(O)c(O)c1)[C@@H](O)C2] | (2S,3S)-2-(3,4-dihydroxyphenyl)-3,5-dihydroxychroman-7-yl 4-phenylbutanoate |

TABLE 2-continued

Illustrative Compounds of the Present Invention.

| S. No. | Structure | IUPAC Name |
|---|---|---|
| 1016 | 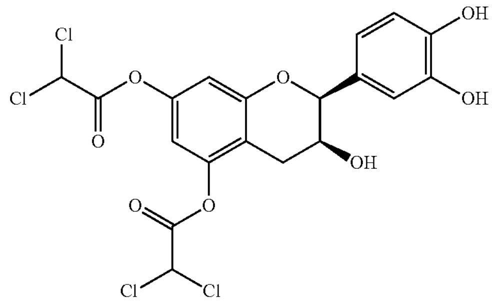 [SMILES: O=C(Oc1cc(OC(=O)C(Cl)Cl)c2c(c1)O[C@@H](c1ccc(O)c(O)c1)[C@@H](O)C2)C(Cl)Cl] | (2S,3S)-2-(3,4-dihydroxyphenyl)-3-hydroxychroman-5,7-diyl bis(2,2-dichloroacetate) |
| 1017 | 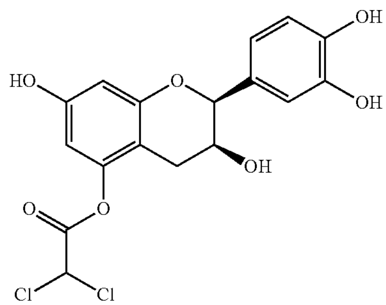 [SMILES: O=C(Oc1cc(O)cc2c1C[C@H](O)[C@H](c1ccc(O)c(O)c1)O2)C(Cl)Cl] | (2S,3S)-2-(3,4-dihydroxyphenyl)-3,7-dihydroxychroman-5-yl 2,2-dichloroacetate |
| 1018 | 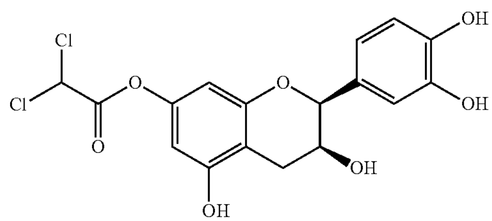 [SMILES: O=C(Oc1cc(O)c2c(c1)O[C@@H](c1ccc(O)c(O)c1)[C@@H](O)C2)C(Cl)Cl] | (2S,3S)-2-(3,4-dihydroxyphenyl)-3,5-dihydroxychroman-7-yl 2,2-dichloroacetate |

The compounds of the present invention include:
i. (2S,3S)-2-(3,4-dihydroxyphenyl)-3,7-dihydroxychroman-5-yl octanoate;
ii. (2S,3S)-2-(3,4-dihydroxyphenyl)-3,5-dihydroxychroman-7-yl octanoate;
iii. (2S,3S)-2-(3,4-dihydroxyphenyl)-3-hydroxychroman-5,7-diyl dioctanoate;
iv. (2S,3S)-2-(3,4-dihydroxyphenyl)-3,7-dihydroxychroman-5-yl heptanoate;
v. (2S,3S)-2-(3,4-dihydroxyphenyl)-3,5-dihydroxychroman-7-yl heptanoate;
vi. (2S,3S)-2-(3,4-dihydroxyphenyl)-3-hydroxychroman-5,7-diyl diheptanoate;
vii. (2S,3S)-2-(3,4-dihydroxyphenyl)-3,7-dihydroxychroman-5-yl decanoate;
viii. (2S,3S)-2-(3,4-dihydroxyphenyl)-3,5-dihydroxychroman-7-yl decanoate;
ix. (2S,3S)-2-(3,4-dihydroxyphenyl)-3-hydroxychroman-5,7-diylbis(decanoate);
x. (2S,3S)-2-(3,4-dihydroxyphenyl)-3-hydroxychroman-5,7-diylbis(2-propylpentanoate);
xi. (2S,3S)-2-(3,4-dihydroxyphenyl)-3,7-dihydroxychroman-5-yl 2-propylpentanoate;
xii. (2S,3S)-2-(3,4-dihydroxyphenyl)-3,5-dihydroxychroman-7-yl 2-propylpentanoate;
xiii. (2S,3S)-2-(3,4-dihydroxyphenyl)-3-hydroxy-5-((3-phenylpropanoyl)oxy)chroman-7-yl 4-phenylbutanoate;
xiv. (2S,3S)-2-(3,4-dihydroxyphenyl)-3,7-dihydroxychroman-5-yl 3-phenylpropanoate;
xv. (2S,3S)-2-(3,4-dihydroxyphenyl)-3,5-dihydroxychroman-7-yl 4-phenylbutanoate;
xvi. (2S,3S)-2-(3,4-dihydroxyphenyl)-3-hydroxychroman-5,7-diylbis(2,2-dichloroacetate)
xvii. (2S,3S)-2-(3,4-dihydroxyphenyl)-3,7-dihydroxychroman-5-yl 2,2-dichloroacetate;
xviii. (2S,3S)-2-(3,4-dihydroxyphenyl)-3,5-dihydroxychroman-7-yl 2,2-dichloroacetate.

C. Synthesis of the Compounds of the Present Invention.

The present invention also relates to a process of preparing the compounds of formula (I). The compounds of present invention may be prepared by the synthetic scheme 1 as here below:

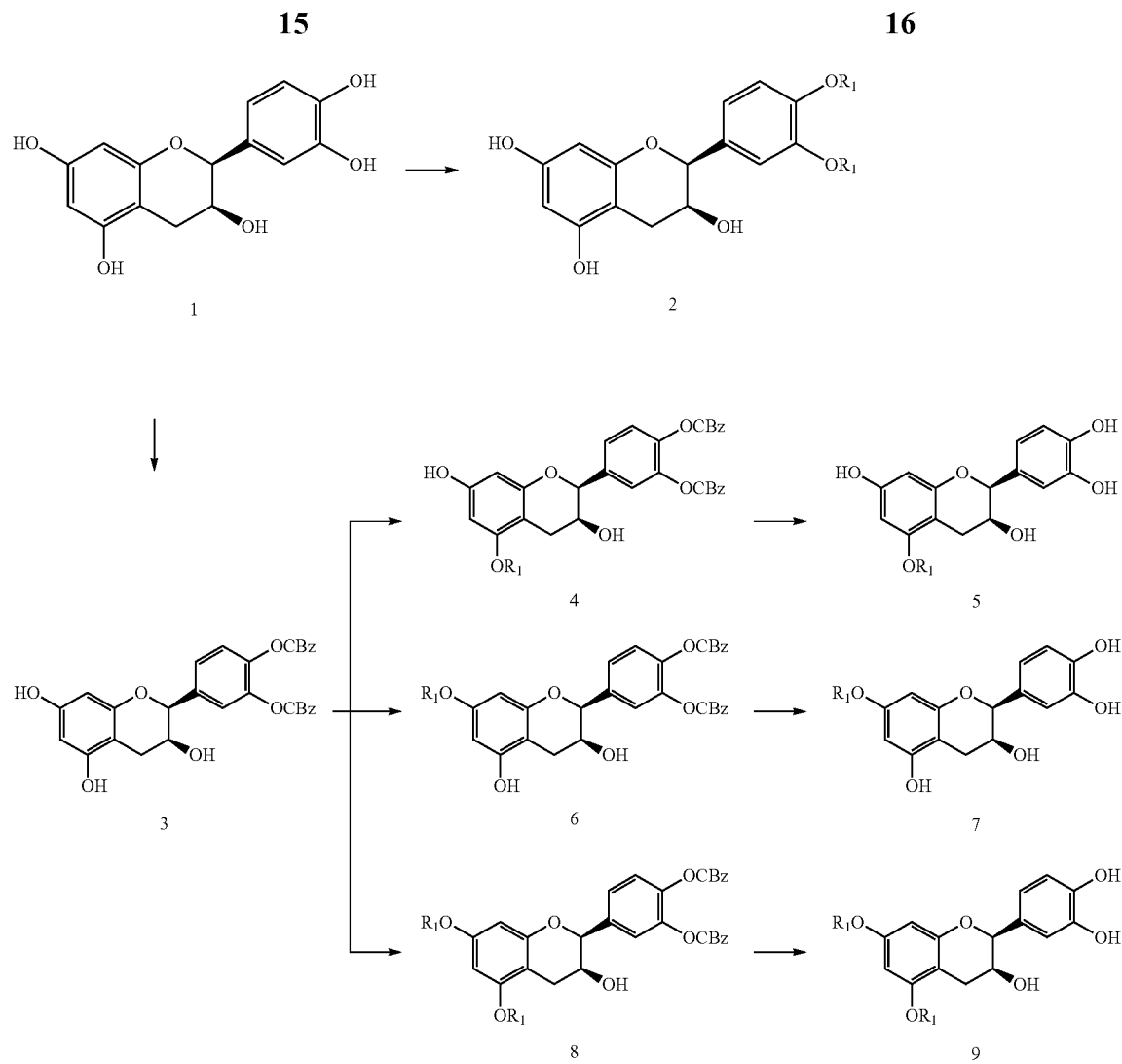

Some of the compound of present interest can be synthesized from (+)-epicatechin (1) by the scheme outline as above. The (+) isomer of epicatechin can be synthesized as mentioned in PCT/IN2012/000052, PCT/IN2014/000061, which are incorporated herein in its entirety. The (+) isomer of a polyphenol e.g. epicatechin when treated with a defined quantity of corresponding acylchloride or carbonyl chloride or carbamoylchlorode in presence of base such as DIPEA or TEA or potassium carbonate in a suitable solvent such as acetonitrile or dichloromethane at a temperature range from 0° C. to refluxing can provide substituted derivatives of interests represented by compound 2.

In other case, a (+) polyphenol such as (+)-epicatechin can be protected using a protecting group known in literature such as CBZ-Cl in presence of a base such as TEA in a solvent such as acetonitrile at temperature ranging from 0° C. to refluxing to give the compound represented by 3. Compound 3 can be derivatized, using different ratios of derivatizing agents to generate analogs with variable $R_1$ as defined above using a base like TEA or DIPEA in a solvent such as acetonitrile at temperature ranging from 0° C. to refluxing to give analogs represented by 4, 6 and 8. Subsequent removal of the CBZ groups of compounds 4, 6 and 8 can give the compounds represented by structures 5, 7 and 9.

The present invention discloses methods involve administering (+)-epicatechin, analogs of (+) epicatechin as set out herein, and chemical derivatives thereof. The present invention discloses diseases and disorders that would benefit from increased mitochondrial activity include diseases or disorders associated with mitochondrial dysfunction.

Without being limited by theory, the compounds of the present invention exhibit superior pharmacokinetic and pharmacodynamic properties in comparison to (+) epicatechin.

The present specification is described by way of certain examples mean for illustration. The examples may not be construed to limit the scope of the invention in any manner.

Example 1: Synthesis of Compounds of the Present Invention

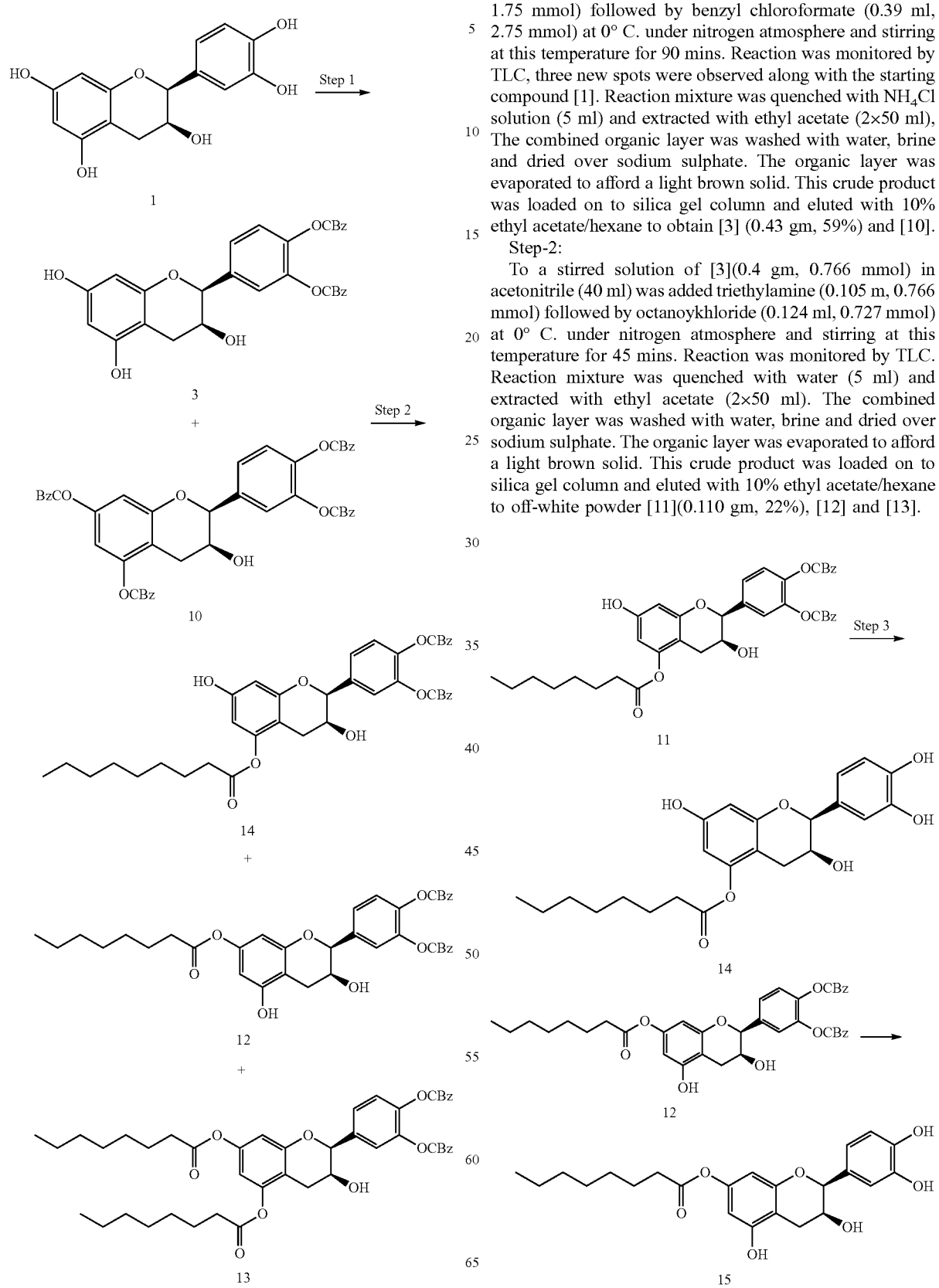

Step-1:
To a stirred solution of [1] (0.4 gm, 1.379 mmol) in acetonitrile (40 ml) was added trimethylamine (0.38 ml, 1.75 mmol) followed by benzyl chloroformate (0.39 ml, 2.75 mmol) at 0° C. under nitrogen atmosphere and stirring at this temperature for 90 mins. Reaction was monitored by TLC, three new spots were observed along with the starting compound [1]. Reaction mixture was quenched with $NH_4Cl$ solution (5 ml) and extracted with ethyl acetate (2×50 ml), The combined organic layer was washed with water, brine and dried over sodium sulphate. The organic layer was evaporated to afford a light brown solid. This crude product was loaded on to silica gel column and eluted with 10% ethyl acetate/hexane to obtain [3] (0.43 gm, 59%) and [10].

Step-2:
To a stirred solution of [3](0.4 gm, 0.766 mmol) in acetonitrile (40 ml) was added triethylamine (0.105 m, 0.766 mmol) followed by octanoykhloride (0.124 ml, 0.727 mmol) at 0° C. under nitrogen atmosphere and stirring at this temperature for 45 mins. Reaction was monitored by TLC. Reaction mixture was quenched with water (5 ml) and extracted with ethyl acetate (2×50 ml). The combined organic layer was washed with water, brine and dried over sodium sulphate. The organic layer was evaporated to afford a light brown solid. This crude product was loaded on to silica gel column and eluted with 10% ethyl acetate/hexane to off-white powder [11](0.110 gm, 22%), [12] and [13].

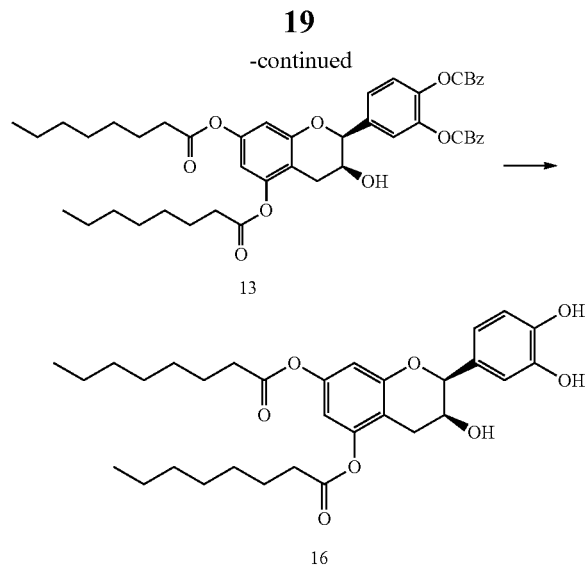

Step-3:

To a stirred solution of [11] (0.050 g. 0.23 mmol) in ethyl acetate (10 ml). was added 10% Pd(OH)$_2$ (0.015 g) and stirred under hydrogen atmosphere at room temperature. The reaction mass was filtered over celite and the solvent was evaporated out to afford light yellow sticky material. This crude product was triturated with ethyl acetate in-pentane to afford yellow sticky material as [14] (0.025 gm, 80%). Compounds 12 and 13 were converted to compounds 15 and 16.

Example 2: Effect of (+) Epicatechin on Triglyceride Level

Animals were placed on High Fat Diet (HFD) until they gain more than 20% of Body weight compared with animals on standard chow and reached glycemia levels ≥200 mg/dL (usually 4-6 weeks). Animals were randomly assigned to Control (obese group) receiving vehicle only (by gavage): n=12; (+)-Epicatechin—orally by gavage: n=10: (−)-Epicatechin—orally by gavage: n=10.

Figure 3:
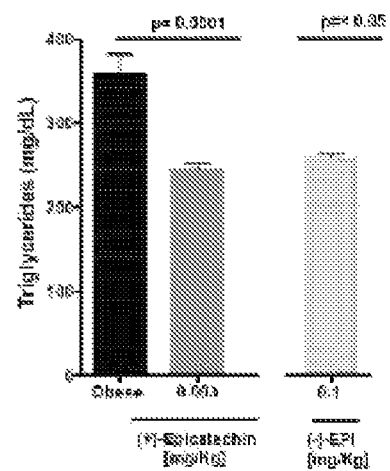
FIG. 3: depicts the activity of the compounds on triglycerides content of livers.

All animals were treated for 15 days and continued under HFD. The results are presented at FIG. 3. Effect on Triglycerides: (+)-Epicatechin (Dose: 0.003 mg/Kg/day shows the same reduction in triglyceride levels as (−)-epicatechin (Dose: 0.1 mg/Kg/day) an improvement of >30 fold.

Example 3: Activity of the Analogue of (+) Epicatechin of the Present Invention The compounds of the present invention were tested for their activity on AMP kinase. The activity on AMP kinase was evaluated by quantitative fluorescent immunoenzymatic assay of AMP kinase phosphorylation status in cultured cells. The 5-AMP-activated protein kinase (AMP kinase) is a key sensor of intracellular energy balance. AMP kinase is activated in response to an increase in the AMP/ATP ratio which can be caused by a number of factors such as muscle contraction, starvation, or hypoxia. AMP kinase is a heterotrimeric protein complex comprising of (63 kDa),—(38 kDa) and—•(38 kDa) subunits. For each subunit, isoforms have been identified (1, 2, 1, 2, 1, 2, 3) which theoretically allow the formation of 12 different proteins. The -subunit contains a serine/threonine kinase domain and the regulatory subunits contain binding sites for AMP and ATP (-subunit) and for glycogen (-subunit). AMP kinase is activated by phosphorylation on Thr-172 within the catalytic domain. AMP binding results in a 2 to 5-fold increase in AMP kinase activity compared to the basal level. Binding of AMP to the -subunit causes allosteric activation of the kinase and induces a conformational change in the kinase domain that protects AMP kinase from dephosphorylation of Thr-172.

BioAssay Systems' cell-based ELISA measure phosphorylated AMP kinase in whole cells and normalizes the signal to the total protein content. The antibody recognizes both -subunits and, thus, can be used for cells from all tissues (human, mouse, rat). This simple and efficient assay eliminates the need for cell lysate preparation and can be used to study AMP kinase regulation in short-term and long-term assays. In this assay, cells grown in 96-well plates are fixed and permeabilized in the wells. AMP kinase phosphorylation (pAMPK) is measured using a fluorescent ELISA followed by total protein measurement in each well. Compound 1001, exhibits AMPK activity at 1 nM.

Example 4: Determination of the Pharmacokinetic Parameters of the Analogue of the Present Invention Female Balb C mice 4 per group after overnight fasting were dosed orally (via gavage) with compound 1 in 5% NMP in normal saline (10 ml/kg). Blood was collected by serial bleeding at 0.16 hr, 0.5 hr, 1 hr, 2 hr, 4 hr, 6 hr, 8 hr in heparinized tubes. Blood samples were centrifuged at 10,000 rpm for 5 min. at 4° C. to obtain the plasma, which were aspirated into separate labeled tubes and stored at −80° C. 400 ng/ml of standard in acetonitrile was used as the drug extraction solvent for extracting drug from plasma. Extraction solvent was added to plasma was vortexed and shaken on shaker for 10 minutes, centrifuged at 10,000 rpm for 10 minutes at 4° C. Supernatant was kept for analysis.

Acetonitrile and plasma calibration curves were generated and percentage of drug recovery from plasma determined. Quantitative analysis was done by liquid chromatography tandem mass spectrometer (API3200 LC-MS/MS). $C_{max}$, $T_{max}$, AUC and $t_{1/2}$ were calculated using Graph Pad PRISM version 5.04 and the results were depicted in Table 3.

TABLE 3

Pharmacokinetic parameters of the compounds of the present invention.

| | PK STUDY (Oral) | | |
|---|---|---|---|
| Compound | AUC (nM * h) | Elimination $t^{1/2}$ (hr) | Dose (mpk) |
| (+) Epicatechin | 683 | 2.13 | 10 |
| 1001 | 2795.70 | 4.50 | 10 |

It may be noted that the compounds of the present invention (1001) are suitable for administration.

The invention claimed is:

1. An analog of (+) epicatechin of the formula (I),

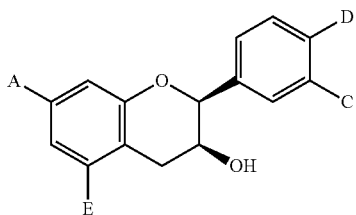

Formula (I)

wherein A and B are independently OR$^1$ and C and D are independently OH, or B is OR$^1$ and A, C and D are independently OH; wherein R$^1$ is independently C$_2$ to C$_{10}$ lower straight or branched chain acyclic or cyclic alkyl, or —C(=O)—(C$_6$-C$_9$ alkyl), or, taken together with the oxygen to which it is attached, is selected from the group consisting of hydroxybutanoate, dichloroacetate, phenyl butanoate, phenyl propionate, and 2-propylpentanoate.

2. The analog of (+) epicatechin of the formula (I), as claimed in claim 1, wherein B is OR$^1$ and A, C and D are independently OH.

3. A compound selected from the group consisting of:
i. (2S,3S)-2-(3,4-dihydroxyphenyl)-3,7-dihydroxychroman-5-yl octanoate;
ii. (2S,3S)-2-(3,4-dihydroxyphenyl)-3,5-dihydroxychroman-7-yl octanoate;
iii. (2S,3S)-2-(3,4-dihydroxyphenyl)-3-hydroxychroman-5,7-diyl dioctanoate;
iv. (2S,3S)-2-(3,4-dihydroxyphenyl)-3,7-dihydroxychroman-5-yl heptanoate;
v. (2S,3S)-2-(3,4-dihydroxyphenyl)-3,5-dihydroxychroman-7-yl heptanoate;
vi. (2S,3S)-2-(3,4-dihydroxyphenyl)-3-hydroxychroman-5,7-diyl diheptanoate;
vii. (2S,3S)-2-(3,4-dihydroxyphenyl)-3,7-dihydroxychroman-5-yl decanoate;
viii. (2S,3S)-2-(3,4-dihydroxyphenyl)-3,5-dihydroxychroman-7-yl decanoate;
ix. (2S,3S)-2-(3,4-dihydroxyphenyl)-3-hydroxychroman-5,7-diyl bis(decanoate);
x. (2S,3S)-2-(3,4-dihydroxyphenyl)-3-hydroxychroman-5,7-diylbis(2-propylpentanoate);
xi. (2S,3S)-2-(3,4-dihydroxyphenyl)-3,7-dihydroxychroman-5-yl 2-propylpentanoate;
xii. (2S,3S)-2-(3,4-dihydroxyphenyl)-3,5-dihydroxychroman-7-yl 2-propylpentanoate;
xiii. (2S,3S)-2-(3,4-dihydroxyphenyl)-3-hydroxy-5-((3-phenylpropanoyl)oxy)chroman-7-yl 4-phenylbutanoate;
xiv. (2S,3S)-2-(3,4-dihydroxyphenyl)-3,7-dihydroxychroman-5-yl 3-phenylpropanoate;
xv. (2S,3S)-2-(3,4-dihydroxyphenyl)-3,5-dihydroxychroman-7-yl 4-phenylbutanoate;
xvi. (2S,3S)-2-(3,4-dihydroxyphenyl)-3-hydroxychroman-5,7-diyl bis(2,2-dichloroacetate);
xvii. (2S,3S)-2-(3,4-dihydroxyphenyl)-3,7-dihydroxychroman-5-yl 2,2-dichloroacetate; and
xviii. (2S,3S)-2-(3,4-dihydroxyphenyl)-3,5-dihydroxychroman-7-yl 2,2-dichloroacetate.

4. The analog of (+) epicatechin of the formula (I), as claimed in claim 1, wherein A and B are independently OR$^1$ and C and D are independently OH.

5. The analog of claim 1, wherein R$^1$, taken together with the oxygen to which it is attached, is selected from the group consisting of hydroxybutanoate, dichloroacetate, phenyl butanoate, phenyl propionate, and 2-propylpentanoate.

6. The analog of claim 2, wherein R$^1$, taken together with the oxygen to which it is attached, is selected from the group consisting of hydroxybutanoate, dichloroacetate, phenyl butanoate, phenyl propionate, and 2-propylpentanoate.

7. The analog of claim 1, wherein R$^1$ is —C(=O)—(C$_6$-C$_9$ alkyl).

8. The analog of claim 2, wherein R$^1$ is —C(=O)—(C$_6$-C$_9$ alkyl).

9. The analog of claim 4, wherein R$^1$, taken together with the oxygen to which it is attached, is selected from the group consisting of hydroxybutanoate, dichloroacetate, phenyl butanoate, phenyl propionate, and 2-propylpentanoate.

10. The analog of claim 4, wherein R$^1$ is —C(=O)—(C$_6$-C$_9$ alkyl).

* * * * *